(12) United States Patent
Burbidge et al.

(10) Patent No.: US 10,583,097 B2
(45) Date of Patent: *Mar. 10, 2020

(54) EXTENSIONAL VISCOSITY TO PROMOTE SAFE SWALLOWING OF FOOD BOLUSES

(75) Inventors: Adam Stewart Burbidge, Arzuer (CH); Jan Engmann, Epalinges (CH); Simina Popa Nita, Morges (CH)

(73) Assignee: Societe des Produits Nestle S.A., Vevey (CH)

( * ) Notice: Subject to any disclaimer, the term of this patent is extended or adjusted under 35 U.S.C. 154(b) by 284 days.

This patent is subject to a terminal disclaimer.

(21) Appl. No.: 14/002,052

(22) PCT Filed: Mar. 1, 2012

(86) PCT No.: PCT/EP2012/053533
§ 371 (c)(1),
(2), (4) Date: Sep. 16, 2013

(87) PCT Pub. No.: WO2012/117065
PCT Pub. Date: Sep. 7, 2012

(65) Prior Publication Data
US 2014/0294787 A1    Oct. 2, 2014

Related U.S. Application Data

(60) Provisional application No. 61/447,745, filed on Mar. 1, 2011, provisional application No. 61/469,852, filed on Mar. 31, 2011, provisional application No. 61/570,879, filed on Dec. 15, 2011.

(30) Foreign Application Priority Data

Dec. 15, 2011    (EP) ..................................... 11193803

(51) Int. Cl.
| | |
|---|---|
| A61K 47/36 | (2006.01) |
| A61K 47/46 | (2006.01) |
| A61K 36/00 | (2006.01) |
| A61K 36/33 | (2006.01) |
| A61K 31/07 | (2006.01) |
| A61K 31/122 | (2006.01) |
| A61K 31/375 | (2006.01) |
| A61K 31/7048 | (2006.01) |
| A61K 33/00 | (2006.01) |
| A61K 35/741 | (2015.01) |
| A61K 35/744 | (2015.01) |
| A61K 35/747 | (2015.01) |
| A23L 29/25 | (2016.01) |
| A23L 29/206 | (2016.01) |
| A23L 33/00 | (2016.01) |
| A23L 29/238 | (2016.01) |
| A61K 36/815 | (2006.01) |
| A61K 35/00 | (2006.01) |

(52) U.S. Cl.
CPC ............ *A61K 31/07* (2013.01); *A23L 29/206* (2016.08); *A23L 29/238* (2016.08); *A23L 29/25* (2016.08); *A23L 33/40* (2016.08); *A61K 31/122* (2013.01); *A61K 31/375* (2013.01); *A61K 31/7048* (2013.01); *A61K 33/00* (2013.01); *A61K 35/741* (2013.01); *A61K 35/744* (2013.01); *A61K 35/747* (2013.01); *A61K 36/815* (2013.01); *A61K 47/36* (2013.01); *A61K 47/46* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 3,664,847 A | * | 5/1972 | Hyldon et al. .......... A23L 7/135 426/620 |
| 5,296,245 A | | 3/1994 | Clarke et al. |
| 6,248,390 B1 | | 6/2001 | Stillman |
| 6,277,395 B1 | * | 8/2001 | Fukui et al. ................... 424/439 |
| 7,008,654 B1 | | 3/2006 | Fuchs et al. |
| 7,115,297 B2 | | 10/2006 | Stillman |
| 7,410,660 B2 | | 8/2008 | Mercati |
| 7,638,150 B2 | | 12/2009 | Holahan |
| 8,802,077 B2 | | 8/2014 | Petit et al. |
| 9,452,150 B2 | | 9/2016 | Ueshima et al. |

(Continued)

FOREIGN PATENT DOCUMENTS

| | | |
|---|---|---|
| CN | 1284838 | 2/2001 |
| JP | 11124342 | 5/1999 |

(Continued)

OTHER PUBLICATIONS

Sengkhamparn et al. "Physicochemical properties of pectins from okra (*Abelmoschus esculentus* (L.) Moench)", Food Hydrocolloids (1): 35-41 Jan. 2010.*

(Continued)

*Primary Examiner* — Emily A Cordas
(74) *Attorney, Agent, or Firm* — K&L Gates LLP

(57) ABSTRACT

Nutritional products having improved cohesiveness of food boluses and methods of making and using same are provided. The nutritional products may include nutritional compositions and high molecular weight, water-soluble polymers such that the nutritional products have extensional viscosities that provide improved cohesiveness to the nutritional products and Trouton ratios of at least 6. Methods of administering such nutritional products to patients having impaired swallowing ability and/or dysphagia are also provided.

7 Claims, No Drawings

(56) References Cited

U.S. PATENT DOCUMENTS

| | | | |
|---|---|---|---|
| 2003/0091613 A1 | 5/2003 | DeWille et al. | |
| 2004/0258823 A1* | 12/2004 | Dufresne | A21D 2/00 426/573 |
| 2007/0224126 A1 | 9/2007 | Dufresne et al. | |

FOREIGN PATENT DOCUMENTS

| | | |
|---|---|---|
| JP | 2000191553 | 7/2000 |
| JP | 2001245613 | 9/2001 |
| JP | 2003189802 | 7/2003 |
| JP | 2005333385 | 12/2005 |
| JP | 2006234444 | 9/2006 |
| JP | 2007105018 | 4/2007 |
| JP | 2007143545 | 6/2007 |
| JP | 2008228729 | 10/2008 |
| JP | 2008263918 | 11/2008 |
| JP | 2009000055 | 1/2009 |
| JP | 2009153441 | 7/2009 |
| JP | 2009278893 | 12/2009 |
| JP | 2010083858 | 4/2010 |
| WO | 0060953 | 10/2000 |
| WO | 03011051 | 2/2003 |
| WO | 2006054886 | 5/2006 |
| WO | WO 2006054886 A1 * | 5/2006 |
| WO | 2007097315 | 8/2007 |
| WO | 2009098469 A1 | 8/2009 |
| WO | 2009113845 A1 | 9/2009 |
| WO | 2009135867 A1 | 11/2009 |
| WO | 2010050541 | 5/2010 |
| WO | 2010122332 | 10/2010 |

OTHER PUBLICATIONS

Chan, Philip Shiu-Kin, et al. "Study of the shear and extensional rheology of casein, waxy maize starch and their mixtures." Food hydrocolloids 21 (5): 716-725, 2007.*

Stintzing et al. "Phytochemical and nutritional significance of cactus pear", European Food Research and Technology 212: 396-407, 2001.*

Ghadimi et al. "Free amino acids of different kinds of milk", American Journal of Clinical Nutrition 13 (1963): 75-81, 1963.*

De Block et al. "Evaluation of two methods for the determination of lactulose in milk." International Dairy Journal 6(2): 217-222, 1996.*

Gronlund et al. "Maternal breast-milk and intestinal bifidobacteria guide the compositional development of the Bifidobacterium microbiota in infants at risk of allergic disease." Clinical & Experimental Allergy 37(12): 1764-1772, 2007.*

Ramsden Chapter 15 "Plant and Algal Gums and Mucilages." Chemical and Functional Properties of Food Saccharides, edited by Piotr Tomasik: 231, 2003 (Year: 2003).*

Guil-Guerrero "Nutritional composition of *Plantago* species (*P. major* L., *P. lanceolata* L., and *P. media* L.)." Ecology of Food and Nutrition 40(5): 481-495, 2001 (Year: 2001).*

Cárdenas et al. "Rheology and aggregation of cactus (*Opuntia ficus-indica*) mucilage in solution", Journal of the Professional Association for Cactus Development 2: 152-159, 1997 (Year: 1997).*

Hussein et al. "Utilization of some plant polysaccharides for improving yoghurt consistency." Annals of Agricultural Sciences 56(2): 97-103, 2011 (Year: 2011).*

Turker et al. "Common mullein (*Verbascum thapsus* L.): recent advances in research." Phytotherapy Research 19(9): 733-739, 2005 (Year: 2005).*

Chinese Office Action for Application No. 201280011111.1, dated Apr. 3, 2015, 9 pages.

Wendin et al. "Objective and quantitative definitions of modified food textures based on sensory and rheological methodology" Food and Nutrition Research, 2010, vol. 54, 11 pages.

Indian Patent Office Communication for Corresponding Application No. 7322/DELNP/2013 dated Jan. 3, 2020 (4 pages).

* cited by examiner

EXTENSIONAL VISCOSITY TO PROMOTE SAFE SWALLOWING OF FOOD BOLUSES

CROSS REFERENCE TO RELATED APPLICATIONS

The present application is a National Stage of International Application No. PCT/EP2012/053533, filed on Mar. 1, 2012, which claims priority to U.S. Provisional Patent Application No. 61/447,745, filed Mar. 1, 2011, U.S. Provisional Patent Application No. 61/469,852, filed Mar. 31, 2011, U.S. Provisional Patent Application No. 61/570,879, filed Dec. 15, 2011, and European Patent Application No. 11193803.1, filed Dec. 15, 2011, the entire contents of which are being incorporated herein by reference.

BACKGROUND

The present disclosure is directed to nutritional products and methods for administering same. More specifically, the present disclosure is directed to nutritional products for promoting safer swallowing of food boluses for patients having swallowing conditions or being impaired thereby.

Dysphagia is the medical term for the symptom of difficulty in swallowing. Epidemiological studies estimate a prevalence rate of 16% to 22% among individuals over 50 years of age.

Esophageal dysphagia affects a large number of individuals of all ages, but is generally treatable with medications and is considered a less serious form of dysphagia. Esophageal dysphagia is often a consequence of mucosal, mediastinal, or neuromuscular diseases. Mucosal (intrinsic) diseases narrow the lumen through inflammation, fibrosis, or neoplasia associated with various conditions (e.g., peptic stricture secondary to gastroesophageal reflux disease, esophageal rings and webs [e.g., sideropenic dysphagia or Plummer-Vinson syndrome], esophageal tumors, chemical injury [e.g., caustic ingestion, pill esophagitis, sclerotherapy for varices], radiation injury, infectious esophagitis, and eosinophilic esophagitis). Mediastinal (extrinsic) diseases obstruct the esophagus by direct invasion or through lymph node enlargement associated with various conditions (tumors [e.g., lung cancer, lymphoma], infections [e.g., tuberculosis, histoplasmosis], and cardiovascular [dilated auricula and vascular compression]). Neuromuscular diseases may affect the esophageal smooth muscle and its innervation, disrupting peristalsis or lower esophageal sphincter relaxation, or both, commonly associated with various conditions (achalasia [both idiopathic and associated with Chagas disease], scleroderma, other motility disorders, and a consequence of surgery [i.e., after fundoplication and anti-reflux interventions]). It is also common for individuals with intraluminal foreign bodies to experience acute esophageal dysphagia.

Oral pharyngeal dysphagia, on the other hand, is a very serious condition and is generally not treatable with medication. Oral pharyngeal dysphagia also affects individuals of all ages, but is more prevalent in older individuals. Worldwide, oral pharyngeal dysphagia affects approximately 22 million people over the age of 50. Oral pharyngeal dysphagia is often a consequence of an acute event, such as a stroke, brain injury, or surgery for oral or throat cancer. In addition, radiotherapy and chemotherapy may weaken the muscles and degrade the nerves associated with the physiology and nervous innervation of the swallow reflex. It is also common for individuals with progressive neuromuscular diseases, such as Parkinson's disease, to experience increasing difficulty in swallowing initiation. Representative causes of oropharyngeal dysphagia include those associated neurological illnesses (brainstem tumors, head trauma, stroke, cerebral palsy, Guillain-Barre syndrome, Huntington's disease, multiple sclerosis, polio, post-polio syndrome, Tardive dyskinesia, metabolic encephalopathies, amyotrophic lateral sclerosis, Parkinson's disease, dementia), infectious illnesses (diphtheria, botulism, Lyme disease, syphilis, mucositis [herpetic, cytomegalovirus, candida, etc.]), autoimmune illnesses (lupus, scleroderma, Sjogren's syndrome), metabolic illnesses (amyloidosis, cushing's syndrome, thyrotoxicosis, Wilson's disease), myopathic illnesses (connective tissue disease, dermatomyositis, myasthenia gravis, myotonic dystrophy, oculopharyngeal dystrophy, polymyositis, sarcoidosis, paraneoplastic syndromes, inflammatory myopathy), iatrogenic illnesses (medication side effects [e.g., chemotherapy, neuroleptics, etc.], post surgical muscular or neurogenic, radiation therapy, corrosive [pill injury, intentional]), and structural illnesses (cricopharyngeal bar, Zenker's diverticulum, cervical webs, oropharyngeal tumors, osteophytes and skeletal abnormalities, congenital [cleft palate, diverticulae, pouches, etc.]).

Dysphagia is not generally diagnosed although the disease has major consequences on patient health and healthcare costs. Individuals with more severe dysphagia generally experience a sensation of impaired passage of food from the mouth to the stomach, occurring immediately after swallowing. Among community dwelling individuals, perceived symptoms may bring patients to see a doctor. Among institutionalized individuals, health care practitioners may observe symptoms or hear comments from the patient or his/her family member suggestive of swallowing impairment and recommend the patient be evaluated by a specialist. As the general awareness of swallowing impairments is low among front-line practitioners, dysphagia often goes undiagnosed and untreated. Yet, through referral to a swallowing specialist (e.g., speech language pathologist), a patient can be clinically evaluated and dysphagia diagnosis can be determined.

The general awareness of swallowing impairments is low among front-line practitioners. Many people (especially those who are elderly) suffer with undiagnosed and untreated swallowing impairments. One reason is that front-line community care practitioners (e.g., general practitioners/geriatricians, home care nurses, physical therapists, etc.) do not typically screen for the condition. If they are aware of the severity of swallowing impairments, they commonly do not use an evidence-based method of screening. Furthermore, office-based assessment of dysphagia rarely occurs.

Severity of dysphagia may vary from: (i) minimal (perceived) difficulty in safely swallowing foods and liquids, (ii) an inability to swallow without significant risk for aspiration or choking, and (iii) a complete inability to swallow. Commonly, the inability to properly swallow foods and liquids may be due to food boluses being broken up into smaller fragments, which may enter the airway or leave unwanted residues in the oropharyngeal and/or esophageal tract during the swallowing process (e.g., aspiration). If enough material enters the lungs, it is possible that the patient may drown on the food/liquid that has built up in the lungs. Even small volumes of aspirated food may lead to bronchopneumonia infection, and chronic aspiration may lead to bronchiectasis and may cause some cases of asthma.

"Silent aspiration," a common condition among elderly, refers to the aspiration of the oropharyngeal contents during sleep. People may compensate for less-severe swallowing impairments by self-limiting the diet. The aging process itself, coupled with chronic diseases such as hypertension or osteoarthritis, predisposes elderly to (subclinical) dysphagia that may go undiagnosed and untreated until a clinical complication such as pneumonia, dehydration, malnutrition (and related complications) occurs. Yet, the differential diagnosis of 'aspiration pneumonia' is not necessarily indicated as a result of current care practices.

The economic costs of dysphagia are associated with hospitalization, re-hospitalization, loss of reimbursement due to pay for performance ("P4P"), infections, rehabilitation, loss of work time, clinic visits, use of pharmaceuticals, labor, care taker time, childcare costs, quality of life, increased need for skilled care. Dysphagia and aspiration impact quality of life, morbidity and mortality. Twelve-month mortality is high (45%) among individuals in institutional care who have dysphagia and aspiration. The economic burden of the clinical consequences arising from lack of diagnosis and early management of dysphagia are significant.

Pneumonia is a common clinical consequence of dysphagia. The condition often requires acute hospitalization and emergency room visits. Among those that develop pneumonia due to aspiration, the differential diagnosis of 'aspiration pneumonia' is not necessarily indicated as a result of current care practices. Based on U.S. healthcare utilization surveys from recent years, pneumonia accounted for over one million hospital discharges and an additional 392,000 were attributable to aspiration pneumonia. Individuals who have general pneumonia as the principal diagnosis have a mean 6 day hospital length of stay and incur over $18,000 in costs for hospital care. It is expected that aspiration pneumonia would carry higher costs for hospital care, based on a mean 8 day length of hospital stay. Pneumonia is life threatening among persons with dysphagia, the odds of death within 3 months is about 50% (van der Steen et al. 2002). In addition, an acute insult such as pneumonia often initiates the downward spiral in health among elderly. An insult is associated with poor intakes and inactivity, resulting in malnutrition, functional decline, and frailty. Specific interventions (e.g., to promote oral health, help restore normal swallow, or reinforce a swallow-safe bolus) would benefit persons at risk for (due to aspiration of oropharyngeal contents, including silent aspiration) or experiencing recurrent pneumonia.

Similar to pneumonia, dehydration is a life-threatening clinical complication of dysphagia. Dehydration is a common co-morbidity among hospitalized individuals with neurodegenerative diseases (thus, likely to have a swallowing impairment). The conditions of Alzheimer's disease, Parkinson's disease, and multiple sclerosis account for nearly 400,000 U.S. hospital discharges annually, and up to 15% of these patients suffer dehydration. Having dehydration as the principal diagnosis is associated with a mean 4 day length of hospital stay and over $11,000 in costs for hospital care. Nevertheless, dehydration is an avoidable clinical complication of dysphagia.

Malnutrition and related complications (e.g., [urinary tract] infections, pressure ulcers, increased severity of dysphagia [need for more-restricted food options, tube feeding, and/or PEG placement and reduced quality of life], dehydration, functional decline and related consequences [falls, dementia, frailty, loss of mobility, and loss of autonomy]) can arise when swallowing impairment leads to fear of choking on food and liquids, slowed rate of consumption, and self-limited food choices. If uncorrected, inadequate nutritional intake exacerbates dysphagia as the muscles that help facilitate normal swallow weaken as physiological reserves are depleted. Malnutrition is associated with having a more than 3-times greater risk of infection. Infections are common in individuals with neurodegenerative diseases (thus, likely to have a chronic swallowing impairment that jeopardizes dietary adequacy). The conditions of Alzheimer's disease, Parkinson's disease, and multiple sclerosis account for nearly 400,000 U.S. hospital discharges annually, and up to 32% of these patients suffer urinary tract infection.

Malnutrition has serious implications for patient recovery. Malnourished patients have longer length of hospital stay, are more likely to be re-hospitalized, and have higher costs for hospital care. Having malnutrition as the principal diagnosis is associated with a mean 8 day length of hospital stay and nearly $22,000 in costs for hospital care. Furthermore, malnutrition leads to unintentional loss of weight and predominant loss of muscle and strength, ultimately impairing mobility and the ability to care for oneself. With the loss of functionality, caregiver burden becomes generally more severe, necessitating informal caregivers, then formal caregivers, and then institutionalization. However, malnutrition is an avoidable clinical complication of dysphagia.

Among persons with neurodegenerative conditions (e.g., Alzheimer's disease), unintentional weight loss (a marker of malnutrition) precedes cognitive decline. In addition, physical activity can help stabilize cognitive health. Thus, it is important to ensure nutritional adequacy among persons with neurodegenerative conditions to help them have the strength and endurance to participate in regular therapeutic exercise and guard against unintentional weight loss, muscle wasting, loss of physical and cognitive functionality, frailty, dementia, and progressive increase in caregiver burden.

Falls and related injuries are a special concern among elderly with neurodegenerative conditions, associated with loss of functionality. Falls are the leading cause of injury deaths among older adults. Furthermore, fall-related injuries among elderly accounted for more than 1.8M U.S. emergency room visits in a recent year. Direct medical costs totaled $179M for fatal and $19.3B for nonfatal fall-related injuries in the period of a year. As an effect of an ambitious non-payment for performance initiative introduced in U.S. hospitals in October 2008, Medicare will no longer pay hospitals for treatment cost of falls and related injuries that occur during the hospital stay. Hospitals will face a loss of about $50,000 for each elderly patient who falls and suffers hip fracture while in hospital care. This new quality initiative is based on the premise that falls are an avoidable medical error. In other words, falls are preventable within reason by applying evidence-based practices including medical nutrition therapy as nutritional interventions are efficacious in the prevention of falls and related injuries (e.g., fractures) among elderly.

Chewing and swallowing difficulties are also recognized risk factors for pressure ulcer development. Pressure ulcers are considered an avoidable medical error, preventable within reason by applying evidence-based practices (including nutritional care, as pressure ulcers are more likely when nutrition is inadequate). Pressure ulcers are a significant burden to the health care system. In U.S. hospitals in 2006, there were 322,946 cases of medical error connected with pressure ulcer development.

The average cost of healing pressure ulcers depends on the stage, ranging from about $1,100 (for stage II) to about $10,000 (for stage III & IV pressure ulcers). Thus, the estimated cost of healing the cases of medical error connected with pressure ulcer development in one year, is in the range of $323M to $3.2B. As an effect of an ambitious non-payment for performance initiative introduced in U.S. hospitals in October 2008, Medicare will no longer pay hospitals for treatment cost of pressure ulcers that develop during the hospital stay (up to $3.2B annually). Pressure ulcers are preventable within reason, in part, by assuring nutritional intakes are adequate. Furthermore, specific interventions including the use of specialized nutritional supplements help reduce the expected time to heal pressure ulcers once they've developed.

In U.S. long-term care facilities, quality of care standards are enforced via the frequent regulatory survey. Surveyors will consider facilities out of compliance when they uncover evidence of actual or potential harm/negative outcomes. The range of penalties include fines, forced closure, as well as lawsuits and settlement fees. The Tag F325 (nutrition) survey considers significant unplanned weight change, inadequate food/fluid intake, impairment of anticipated wound healing, failure to provide a therapeutic diet as ordered, functional decline, and fluid/electrolyte imbalance as evidence for providing sub-standard [Nutrition] care. The Tag F314 (pressure ulcers) survey mandates that the facility must ensure that a resident who is admitted without pressure ulcers does not develop pressure ulcers unless deemed unavoidable. In addition, that a resident having pressure ulcers receives necessary treatment and services to promote healing, prevent infection and prevent new pressure ulcers from developing.

Considering the prevalence of dysphagia, possible complications related thereto, and the costs associated with same, it would be beneficial to provide nutritional products that promote safer swallowing of food boluses in patients suffering from such swallowing disorders. Such nutritional products would improve the lives of a large and growing number of persons with swallowing impairments. Specific interventions (e.g., to promote oral health, help restore normal swallow, or reinforce a swallow-safe bolus) can enable persons to eat orally (vs. being tube fed and/or requiring PEG placement) and experience the psycho-social aspects of food associated with general well being while guarding against the potentially negative consequences that result from lack of adequate swallowing ability. Improvements in the intake of nutrition by dysphagic patients may also enable such patients to swallow a wider variety of food and beverage products safely and comfortably, which may lead to an overall healthier condition of the patient and prevent further health-related decline.

Several prior art documents disclose compositions for use in dysphagia treatments, none of which however provides sufficiently viscous properties to efficiently promote safer swallowing of food boluses.

Chan et al. (see Food Hydrocolloids 21, p. 716-725 (2007)), for example, presents a study of the shear and extensional rheology of casein, waxy maize starch and their mixtures for industrial biopolymers. In this article, Chan et al. mention that the shear and uniaxial extensional flow behaviour of aqueous casein and phosphate waxy maize starch systems was measured as a function of the deformation rate, biopolymer concentration and the temperature. However, Chan et al. do not provide any further applications such as treatment of dysphagia or details as to which properties a suitable composition shall have to effectively promote safer swallowing.

US 2011/217442 (filed on 8 Mar. 2010 by CP Kelco US) mentions compositions and methods for producing consumables for patients with dysphagia. In this context, US 2011/217442 mentions compositions including a modified xanthan gum in an amount suitable to provide a viscous, free-flowing solution having gel-like properties. US 2011/217442 does not provide any further components or information on specific viscosities suitable to promote safer swallowing.

WO 2011/056487 (filed on 25 Oct. 2010 by Nestec S.A) deals with stable thickener formulations and nutritional compositions comprising such a stable thickener formulation, e.g. a stable thickener formulation comprising from about 0.015 percent to about 0.05 percent by weight of carrageenan and from about 1.2 percent to about 4.0 percent by weight of starch. The stable thickener formulation can be used in nutritional compositions used to treat a variety of physiological conditions. WO 2011/056487 does not provide any further components or rheological requirements suitable to promote safer swallowing.

In view of the prior art, there remains a need to provide improved nutritional products which promote safer swallowing of food boluses and methods for administering same to patients having swallowing conditions or being impaired thereby.

SUMMARY

The present disclosure is related to nutritional products and methods for administering same. More specifically, the present disclosure is related to nutritional products for promoting safer swallowing of food boluses. In a general embodiment, a nutritional product including a nutritional composition and a food grade polymer capable of increasing an extensional viscosity of the composition such that the nutritional product has a Trouton ratio that is at least 6, preferably from about 6 to about 15. In an embodiment, the Trouton ratio is about 10. In another embodiment, the inventive nutritional product has an extensional viscosity that is greater than 100 milli Pascal seconds ("mPas").

In an embodiment, the food grade polymer is selected from the group consisting of plant-extracted gums, plant-derived mucilages and combinations thereof. The plant-extracted gums may further be selected from the group consisting of okra gum, konjac mannan, tara gum, locust bean gum, guar gum, fenugreek gum, tamarind gum, cassia gum, acacia gum, gum ghatti, pectins, cellulosics, tragacanth gum, karaya gum, or any combinations thereof. In a preferred embodiment, the plant-extracted gum is okra gum. Further, the plant-derived mucilages may be selected from the group consisting of cactus mucilage (*Ficus indica*), psyllium mucilage (*Plantago ovata*), mallow mucilage (*Malva sylvestris*), flax seed mucilage (*Linum usitatissimum*), marshmallow mucilage (*Althaea officinalis*), ribwort mucilage (*Plantago lanceolata*), mullein mucilage (*Verbascum*), cetraria mucilage (*Lichen islandicus*), or any combinations thereof. In a preferred embodiment, the plant-derived mucilage is cactus mucilage (*Ficus indica*). It is particularly preferred that the food grade polymer is selected from okra gum and/or cactus mucilage (*Ficus indica*), or a combination thereof. In a further preferred embodiment, the plant-extracted gums and/or the inventive nutritional product do not contain starch, such as waxy maize starch, xanthan gum, modified xanthan gum such as non-pyruvylated xanthan gum or reduced-pyruvylated xanthan gum, carageenan, or a combination thereof. Preferably, it does not contain a combination of starch and carrageenan or a combination of casein and waxy maize starch.

In an embodiment, the inventive nutritional products include a prebiotic. The prebiotic is selected from the group consisting of fructooligosaccharides, inulin, lactulose, galactooligosaccharides, acacia gum, soyoligosaccharides, xylooligosaccharides, isomaltooligosaccharides, gentiooligosaccharides, lactosucrose, glucooligosaccharides, pecticoligosaccharides, resistant starches, sugar alcohols or combinations thereof.

In an embodiment, the inventive nutritional products include a probiotic. The probiotic is selected from the group consisting of Saccharomyces, Debaromyces, Candida, Pichia, Torulopsis, Aspergillus, Rhizopus, Mucor, Penicillium, Torulopsis, *Bifidobacterium*, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus, *Lactobacillus* or combinations thereof.

In an embodiment, the inventive nutritional products include an amino acid. The amino acid is selected from the group consisting of Isoleucine, Alanine, Leucine, Asparagine, Lysine, Aspartate, Methionine, Cysteine, Phenylalanine, Glutamate, Threonine, Glutamine, Tryptophan, Citrulline, Glycine, Valine, Proline, Serine, Tyrosine, Arginine, Histidine or combinations thereof.

In an embodiment, the inventive nutritional product includes a fatty acid component of a fish oil selected from the group consisting of docosahexaenoic acid ("DHA"), eicosapentaenoic acid ("EPA"), or combinations thereof. DHA and EPA may also be derived from krill, algae, modified plants, flaxseed, walnut, etc. Certain fatty acids (e.g., 18:4 fatty acids) may also be readily converted to DHA and/or EPA. The nutritional product may further include α-linolenic acid.

In an embodiment, the inventive nutritional products include a phytonutrient. The phytonutrient is selected from the group consisting of quercetin, curcumin, limonin or combinations thereof.

In an embodiment, the inventive nutritional products include an antioxidant. The antioxidant is selected from the group consisting of vitamin A, carotenoids, vitamin C, vitamin E, selenium, flavonoids, Lactowolfberry, wolfberry, polyphenols, lycopene, lutein, lignan, coenzyme Q10, glutathione or combinations thereof.

In an embodiment, the inventive nutritional product is in an administrable form selected from the group consisting of pharmaceutical formulations, nutritional formulations, dietary supplements, functional food and beverage products or combinations thereof. The inventive nutritional product may be present in a liquid, a semi-liquid or a semi-solid state. Alternatively, the nutritional product as defined herein may be provided in dry form, such as a powder, wherein, upon adding water or an appropriate liquid as defined herein, the nutritional product as defined herein can be reconstituted to exhibit a Trouton ratio that is at least 6, and that is preferably from about 6 to about 15.

In yet another embodiment, methods for making a nutritional product are provided. The methods include providing a nutritional composition and adding a food grade polymer to the nutritional composition to form a nutritional product having a Trouton ratio that is at least 6, and that is preferably from about 6 to about 15. In an embodiment, the Trouton ratio may be about 10. In another embodiment, the nutritional product may have an extensional viscosity that is greater than 100 milli Pascal seconds ("mPas"). Preferably, the nutritional product is as defined herein.

In still yet another embodiment, methods for improving the cohesiveness of a nutritional product are provided. The methods include adding to a nutritional composition a food grade polymer to form a nutritional product, preferably as defined herein, the food grade polymer capable of improving a cohesiveness of the nutritional composition such that the nutritional product does not break-up during consumption of the nutritional product. In an embodiment, a Trouton ratio of the nutritional product is at least 6, and preferably from about 6 to about 15. In a particularly preferred embodiment, the Trouton ratio may be about 10. In another embodiment, the nutritional product may have an extensional viscosity that is greater than 100 milli Pascal seconds ("mPas").

In still yet another embodiment, methods for promoting safe swallowing of food boluses are provided. The methods include adding to a nutritional composition a food grade polymer to form a nutritional product, preferably as defined herein, the food grade polymer capable of improving a cohesiveness of the nutritional composition such that the nutritional product does not break-up during consumption of the nutritional product, and administering the nutritional product to a patient in need of same. In an embodiment, a Trouton ratio of the nutritional product is at least 6, and preferably from about 6 to about 15. In a particularly preferred embodiment, the Trouton ratio may be about 10. In another embodiment, the nutritional product may have an extensional viscosity that is greater than 100 milli Pascal seconds ("mPas"). The viscosity may be determined using methods known to a person skilled in the art.

In another embodiment, methods for treating a patient having a swallowing disorder are provided. The methods include administering to a patient in need of same a nutritional product, preferably as defined herein, comprising a nutritional composition and a food grade polymer, the nutritional product having a Trouton ration that is at least 6, and preferably from about 6 to about 15. In a preferred embodiment, the Trouton ratio may be about 10. In another embodiment, the nutritional product may have an extensional viscosity that is greater than 100 milli Pascal seconds ("mPas").

In an embodiment, the food grade polymer is selected from the group consisting of plant-extracted gums, plant-derived mucilages and combinations thereof. The plant-extracted gums may further be selected from the group consisting of okra gum, konjac mannan, tara gum, locust bean gum, guar gum, fenugreek gum, tamarind gum, cassia gum, acacia gum, gum ghatti, pectins, cellulosics, tragacanth gum, karaya gum, or any combinations thereof. In a preferred embodiment, the plant-extracted gum is okra gum. The plant-derived mucilages may be selected from the group consisting of cactus mucilage (*Ficus indica*), psyllium mucilage (*Plantago ovata*), mallow mucilage (*Malva sylvestris*), flax seed mucilage (*Linum usitatissimum*), marshmallow mucilage (*Althaea officinalis*), ribwort mucilage (*Plantago lanceolata*), mullein mucilage (*Verbascum*), cetraria mucilage (*Lichen islandicus*), or any combinations thereof. In a preferred embodiment, the plant-derived mucilage is cactus mucilage (*Ficus indica*). It is particularly preferred that the food grade polymer is selected from okra gum and/or cactus mucilage (*Ficus indica*), or a combination thereof. In a further preferred embodiment, the plant-extracted gums and/or the inventive nutritional product do not contain starch, such as waxy maize starch, xanthan gum, modified xanthan gum such as non-pyruvylated xanthan gum or reduced-pyruvylated xanthan gum, carageenan, or a combination thereof. Preferably, it does not contain a combination of starch and carrageenan or a combination of casein and waxy maize starch.

An advantage of the present disclosure is to provide improved nutritional products.

Another advantage of the present disclosure is to provide nutritional products having improved cohesiveness.

Yet another advantage of the present disclosure is to provide improved nutritional products for patients having dysphagia.

Still yet another advantage of the present disclosure is to provide methods for treating patients having dysphagia.

Another advantage of the present disclosure is to provide methods for improving the cohesiveness of a composition.

Yet another advantage of the present disclosure is to provide methods for promoting safe swallowing of food boluses.

Additional features and advantages are described herein, and will be apparent from the following detailed description.

DETAILED DESCRIPTION

As used herein, "about" is understood to refer to numbers in a range of numerals. Moreover, all numerical ranges herein should be understood to include all integer, whole or fractions, within the range.

As used herein the term "amino acid" is understood to include one or more amino acids. The amino acid can be, for example, alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, or combinations thereof.

As used herein, "animal" includes, but is not limited to, mammals, which include but is not limited to, rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals that are capable of the effect exhibited or intended to be exhibited by the context of the passage.

As used herein, the term "antioxidant" is understood to include any one or more of various substances such as beta-carotene (a vitamin A precursor), vitamin C, vitamin E, and selenium) that inhibit oxidation or reactions promoted by Reactive Oxygen Species ("ROS") and other radical and non-radical species. Additionally, antioxidants are molecules capable of slowing or preventing the oxidation of other molecules. Non-limiting examples of antioxidants include carotenoids, coenzyme Q10 ("CoQ10"), flavonoids, glutathione Goji (wolfberry), hesperidin, lactowolfberry, lignan, lutein, lycopene, polyphenols, selenium, vitamin A, vitamin $B_1$, vitamin $B_6$, vitamin $B_{12}$, vitamin C, vitamin D, vitamin E, zeaxanthin, or combinations thereof.

As used herein, "effective amount" is an amount that prevents a deficiency, treats a disease or medical condition as mentioned herein in an individual or, more generally, reduces symptoms, manages progression of the diseases mentioned herein or provides a nutritional, physiological, or medical benefit to the individual. A treatment can be patient- or doctor-related.

While the terms "individual" and "patient" are often used herein to refer to a human, the invention is not so limited. Accordingly, the terms "individual" and "patient" refer to any animal, mammal or human having or at risk for a medical condition that can benefit from the treatment. More preferably, the term "patient" as defined herein, is used for an animal, mammal or human, typically suffering from a disease as defined herein.

As used herein, non-limiting examples of sources of ω-3 fatty acids such α-linolenic acid ("ALA"), docosahexaenoic acid ("DHA") and eicosapentaenoic acid ("EPA") include fish oil, krill, poultry, eggs, or other plant or nut sources such as flax seed, walnuts, almonds, algae, modified plants, etc.

As used herein, "food grade micro-organisms" means micro-organisms that are used and generally regarded as safe for use in food.

As used herein, "mammal" includes, but is not limited to, rodents, aquatic mammals, domestic animals such as dogs and cats, farm animals such as sheep, pigs, cows and horses, and humans. Wherein the term "mammal" is used, it is contemplated that it also applies to other animals that are capable of the effect exhibited or intended to be exhibited by the mammal.

The term "microorganism" is meant to include the bacterium, yeast and/or fungi, a cell growth medium with the microorganism, or a cell growth medium in which microorganism was cultivated.

As used herein, the term "minerals" is understood to include boron, calcium, chromium, copper, iodine, iron, magnesium, manganese, molybdenum, nickel, phosphorus, potassium, selenium, silicon, tin, vanadium, zinc, or combinations thereof.

As used herein, a "non-replicating" microorganism means that no viable cells and/or colony forming units can be detected by classical plating methods. Such classical plating methods are summarized in the microbiology book: James Monroe Jay, et al., *Modern food microbiology,* 7th edition, Springer Science, New York, N.Y. p. 790 (2005). Typically, the absence of viable cells can be shown as follows: no visible colony on agar plates or no increasing turbidity in liquid growth medium after inoculation with different concentrations of bacterial preparations ('non replicating' samples) and incubation under appropriate conditions (aerobic and/or anaerobic atmosphere for at least 24 h). For example, bifidobacteria such as *Bifidobacterium longum, Bifidobacterium lactis* and *Bifidobacterium breve* or lactobacilli, such as *Lactobacillus paracasei* or *Lactobacillus rhamnosus,* may be rendered non-replicating by heat treatment, in particular low temperature/long time heat treatment.

As used herein, a "nucleotide" is understood to be a subunit of deoxyribonucleic acid ("DNA") or ribonucleic acid ("RNA"). It is an organic compound made up of a nitrogenous base, a phosphate molecule, and a sugar molecule (deoxyribose in DNA and ribose in RNA). Individual nucleotide monomers (single units) are linked together to form polymers, or long chains. Exogenous nucleotides are specifically provided by dietary supplementation. The exogenous nucleotide can be in a monomeric form such as, for example, 5'-Adenosine Monophosphate ("5'-AMP"), 5'-Guanosine Monophosphate ("5'-GMP"), 5'-Cytosine Monophosphate ("5'-CMP"), 5'-Uracil Monophosphate ("5'-UMP"), 5'-Inosine Monophosphate ("5'-IMP"), 5'-Thymine Monophosphate ("5'-TMP"), or combinations thereof. The exogenous nucleotide can also be in a polymeric form such as, for example, an intact RNA. There can be multiple sources of the polymeric form such as, for example, yeast RNA.

"Nutritional compositions," as used herein, are understood to include any number of optional additional ingredients, including conventional food additives, for example one or more, acidulants, additional thickeners, buffers or agents for pH adjustment, chelating agents, colorants, emulsifies, excipient, flavor agent, mineral, osmotic agents, a pharmaceutically acceptable carrier, preservatives, stabilizers, sugar, sweeteners, texturizers, and/or vitamins. The optional ingredients can be added in any suitable amount.

As used herein the term "patient" is understood to include an animal, especially a mammal, and more especially a human that is receiving or intended to receive treatment, as it is herein defined. A patient may be generally of any age, e.g. a young patient (e.g. between about 0 and 30 years), a medium aged patient (e.g. between about 30 and 50 years) or an elderly patient. More preferably, a patient is an elderly patient, preferably an elderly mammal or human patient, more preferably a human over 50 years of age, even more preferably a human over 60 years of age and most preferably a human over 70 years of age, receiving or intended to receive a treatment, preferably against a disease as defined herein.

As used herein, "phytochemicals" or "phytonutrients" are non-nutritive compounds that are found in many foods. Phytochemicals are functional foods that have health benefits beyond basic nutrition, and are health promoting compounds that come from plant sources. "Phytochemicals" and "Phytonutrients" refers to any chemical produced by a plant that imparts one or more health benefit on the user. Non-limiting examples of phytochemicals and phytonutrients include those that are:

i) phenolic compounds which include monophenols (such as, for example, apiole, carnosol, carvacrol, dillapiole, rosemarinol); flavonoids (polyphenols) including flavonols (such as, for example, quercetin, fingerol, kaempferol, myricetin, rutin, isorhamnetin), flavanones (such as, for example, fesperidin, naringenin, silybin, eriodictyol), flavones (such as, for example, apigenin, tangeritin, luteolin), flavan-3-ols (such as, for example, catechins, (+)-catechin, (+)-gallocatechin, (−)-epicatechin, (−)-epigallocatechin, (−)-epigallocatechin gallate (EGCG), (−)-epicatechin 3-gallate, theaflavin, theaflavin-3-gallate, theaflavin-3'-gallate, theaflavin-3,3'-digallate, thearubigins), anthocyanins (flavonals) and anthocyanidins (such as, for example, pelargonidin, peonidin, cyanidin, delphinidin, malvidin, petunidin), isoflavones (phytoestrogens) (such as, for example, daidzein (formononetin), genistein (biochanin A), glycitein), dihydroflavonols, chalcones, coumestans (phytoestrogens), and Coumestrol; Phenolic acids (such as: Ellagic acid, Gallic acid, Tannic acid, Vanillin, curcumin); hydroxycinnamic acids (such as, for example, caffeic acid, chlorogenic acid, cinnamic acid, ferulic acid, coumarin); lignans (phytoestrogens), silymarin, secoisolariciresinol, pinoresinol and lariciresinol); tyrosol esters (such as, for example, tyrosol, hydroxytyrosol, oleocanthal, oleuropein); stilbenoids (such as, for example, resveratrol, pterostilbene, piceatannol) and punicalagins;

ii) terpenes (isoprenoids) which include carotenoids (tetraterpenoids) including carotenes (such as, for example, α-carotene, β-carotene, γ-carotene, δ-carotene, lycopene, neurosporene, phytofluene, phytoene), and xanthophylls (such as, for example, canthaxanthin, cryptoxanthin, aeaxanthin, astaxanthin, lutein, rubixanthin); monoterpenes (such as, for example, limonene, perillyl alcohol); saponins; lipids including: phytosterols (such as, for example, campesterol, beta sitosterol, gamma sitosterol, stigmasterol), tocopherols (vitamin E), and ω-3, -6, and -9 fatty acids (such as, for example, gamma-linolenic acid); triterpenoid (such as, for example, oleanolic acid, ursolic acid, betulinic acid, moronic acid);

iii) betalains which include Betacyanins (such as: betanin, isobetanin, probetanin, neobetanin); and betaxanthins (non glycosidic versions) (such as, for example, indicaxanthin, and vulgaxanthin);

iv) organosulfides, which include, for example, dithiolthiones (isothiocyanates) (such as, for example, sulphoraphane); and thiosulphonates (allium compounds) (such as, for example, allyl methyl trisulfide, and diallyl sulfide), indoles, glucosinolates, which include, for example, indole-3-carbinol; sulforaphane; 3,3'-diindolylmethane; sinigrin; allicin; alliin; allyl isothiocyanate; piperine; syn-propanethial-S-oxide;

v) protein inhibitors, which include, for example, protease inhibitors;

vi) other organic acids which include oxalic acid, phytic acid (inositol hexaphosphate); tartaric acid; and anacardic acid; or vii) combinations thereof.

As used in this disclosure and the appended claims, the singular forms "a," "an" and "the" include plural referents unless the context clearly dictates otherwise. Thus, for example, reference to "a polypeptide" includes a mixture of two or more polypeptides, and the like.

As used herein, a "prebiotic" is a food substance that selectively promotes the growth of beneficial bacteria or inhibits the growth or mucosal adhesion of pathogenic bacteria in the intestines. They are not inactivated in the stomach and/or upper intestine or absorbed in the gastrointestinal tract of the person ingesting them, but they are fermented by the gastrointestinal microflora and/or by probiotics. Prebiotics are, for example, defined by Glenn R. Gibson and Marcel B. Roberfroid, *Dietary Modulation of the Human Colonic Microbiota: Introducing the Concept of Prebiotics*, J. Nutr. 1995 125: 1401-1412. Non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, or their hydrolysates, or combinations thereof.

As used herein, probiotic micro-organisms (hereinafter "probiotics") are food-grade microorganisms (alive, including semi-viable or weakened, and/or non-replicating), metabolites, microbial cell preparations or components of microbial cells that could confer health benefits on the host when administered in adequate amounts, more specifically, that beneficially affect a host by improving its intestinal microbial balance, leading to effects on the health or well-being of the host. See, Salminen S, Ouwehand A. Benno Y. et al., *Probiotics: how should they be defined?*, Trends Food Sci. Technol. 1999:10, 107-10. In general, it is believed that these micro-organisms inhibit or influence the growth and/or metabolism of pathogenic bacteria in the intestinal tract. The probiotics may also activate the immune function of the host. For this reason, there have been many different approaches to include probiotics into food products. Non-limiting examples of probiotics include *Aerococcus, Aspergillus, Bacillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or combinations thereof.

The terms "protein," "peptide," "oligopeptides" or "polypeptide," as used herein, are understood to refer to any composition that includes, a single amino acids (monomers), two or more amino acids joined together by a peptide bond (dipeptide, tripeptide, or polypeptide), collagen, precursor, homolog, analog, mimetic, salt, prodrug, metabolite, or fragment thereof or combinations thereof. For the sake of clarity, the use of any of the above terms is interchangeable unless otherwise specified. It will be appreciated that polypeptides (or peptides or proteins or oligopeptides) often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Among the known modifications which may be present in polypeptides of the present invention include, but are not limited to, acetylation, acylation, ADP-ribosylation, amidation, covalent attachment of a flavanoid or a heme moiety, covalent attachment of a polynucleotide or polynucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycation, glycosylation, glycosylphosphatidyl inositol ("GPI") membrane anchor formation, hydroxylation, iodination, methylation, myristoylation, oxidation, proteolytic processing, phosphorylation, prenylation, racemization, selenoylation, sulfation, transfer-RNA mediated addition of amino acids to polypeptides such as arginylation, and ubiquitination. The term "protein" also includes "artificial proteins" which refers to linear or non-linear polypeptides, consisting of alternating repeats of a peptide.

Non-limiting examples of proteins include dairy based proteins, plant based proteins, animal based proteins and artificial proteins. Dairy based proteins include, for example, casein, caseinates (e.g., all forms including sodium, calcium, potassium caseinates), casein hydrolysates, whey (e.g., all forms including concentrate, isolate, demineralized), whey hydrolysates, milk protein concentrate, and milk protein isolate. Plant based proteins include, for example, soy protein (e.g., all forms including concentrate and isolate), pea protein (e.g., all forms including concentrate and isolate), canola protein (e.g., all forms including concentrate and isolate), other plant proteins that commercially are wheat and fractionated wheat proteins, corn and it fractions including zein, rice, oat, potato, peanut, green pea powder, green bean powder, and any proteins derived from beans, lentils, and pulses. Animal based proteins may be selected from the group consisting of beef, poultry, fish, lamb, seafood, or combinations thereof.

All dosage ranges contained within this application are intended to include all numbers, whole or fractions, contained within said range.

As used herein, a "synbiotic" is a supplement that contains both a prebiotic and a probiotic that work together to improve the microflora of the intestine.

As used herein, the terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition, such as nitrogen imbalance or muscle loss. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition. More preferably, the term "treatment" in the context of the present invention refers to prevention and/or treatment of swallowing disorders, preferably prevention and/or treatment of dysphagia, but also prevention and/or treatment of malnourishment or undernourishment associated with dysphagia, preferably as mentioned above, such as e.g. silent aspiration, pneumonia, aspiration pneumonia, dehydration, pressure ulcers, etc. Treatment also may be accomplished with regard to dysphagia patients or patients highly susceptible of dysphagia or at risk of developing dysphagia, such as patients suffering from stroke, Parkinson's, Alzheimer's, Brain Damage and Multiple Sclerosis.

As used herein the term "vitamin" is understood to include any of various fat-soluble or water-soluble organic substances (non-limiting examples include vitamin A, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), and Vitamin B12 (various cobalamins; commonly cyanocobalamin in vitamin supplements), vitamin C, vitamin D, vitamin E, vitamin K, folic acid and biotin) essential in minute amounts for normal growth and activity of the body and obtained naturally from plant and animal foods or synthetically made, pro-vitamins, derivatives, analogs.

The present disclosure relates to nutritional products for promoting safer swallowing of food boluses for patients suffering from swallowing disorders including, for example, dysphagia. The present disclosure also relates to methods for providing treatment for a patient having a swallowing disorder.

The normal swallowing of a human (or mammal) involves three distinct phases which are interdependent and well coordinated: (i) the oral, (ii) the pharyngeal, and (iii) the esophageal phases. In the oral phase, which is under voluntary control, food that has been chewed and mixed with saliva is formed into a bolus for delivery by voluntary tongue movements to the back of the mouth, into the pharynx. The pharyngeal phase is involuntary and is triggered by food/liquid bolus passing through the faucial pillars into the pharynx. Contraction of the three constrictors of the pharynx propel the bolus towards the upper esophageal sphincter. Simultaneously, the soft palate closes the nasopharynx. The larynx moves upwards to prevent food or liquid passing into the airway, which is aided by the backward tilt of the epiglottis and closure of the vocal folds. The esophageal phase is also involuntary and starts with the relaxation of the upper esophageal sphincter followed by peristalsis, which pushes the bolus down to the stomach.

Dysphagia refers to the symptom of difficulty in swallowing. The following general causes of dysphagia have been identified:
a) A decreased ability to swallow
b) Tongue not exerting enough pressure on soft palate
  i) Iatrogenic
    (1) Surgical removal of part of the tongue or soft palate
      (a) Treatment for snoring or sleep apnea
      (b) Resection due to tumor (malignant or benign)
  ii) Genetic
    (1) Hypoplasia of the tongue and/or soft palate
    (2) Hypo or lack of innervation to tongue and/or soft palate
  iii) Traumatic
    (1) Tissue damage
    (2) Deinnervation/hypoinnervation
  iv) Neurologic
    (1) Local deinnervation/hypoinnervation
    (2) CNS
      (a) Post stroke
      (b) Demylination
c) Abnormal epiglottis behavior
  i) Not closing and opening at proper times
    (1) Opening too early
    (2) Not closing in time
      (a) Delayed closing
  ii) Not closing completely (insufficient flexibility—atrophy)

The consequences of untreated or poorly managed oral pharyngeal dysphagia can be severe, including dehydration, malnutrition leading to dysfunctional immune response, and reduced functionality, airway obstruction with solid foods (choking), and airway aspiration of liquids and semi-solid foods, promoting aspiration pneumonia and/or pneumonitis. Severe oral pharyngeal dysphagia may require nutrition to be supplied by tube feeding.

Mild to moderate oral pharyngeal dysphagia may require the texture of foods to be modified in order to minimize the likelihood of choking or aspiration. This may include the thickening of liquids and/or pureeing of solid foods, both of which have been shown to be the most effective means of preventing choking and aspiration during the eating process. Thickened liquids are designed to have three properties: (i) a more cohesive bolus that can be maintained throughout the action of swallowing, (ii) slower delivery to the throat, thereby compensating for the increased period in which the swallowing reflexes prepare for the thickened liquid, and (iii) provide greater density to increase awareness of the presence of food or liquid bolus in the mouth.

Improving an individual's ability and efficiency to swallow improves the individual's safety through reduced risk of pulmonary aspiration. An efficient swallow may permit greater independence from feeding assistance and/or reduced length of time spent in feeding-assistance during meal consumption. Efficient swallowing also reduces the viscosity of liquids required for safety (e.g., pudding, honey and nectar thickness products) and may also limit the use of texture-modified foods. All of these previously described factors are aimed at improving an individual's quality of life.

In a general embodiment, the present disclosure provides nutritional products for promoting safer swallowing of food boluses in patients with swallowing disorders (e.g., dysphagic patients) by preventing bolus penetration and aspiration through modification of rheological properties of foods and beverages. Rheology is the study of the flow of matter, primarily in the liquid state but also as soft solids or solids under conditions in which they respond with plastic flow rather than deforming elastically in response to an applied force. The flow of substances cannot generally be characterized by a single value of viscosity, although viscosity measurements at specific temperatures can provide valuable information about a material's properties. Rheological studies are generally performed using rheometers, which generally impose a specific stress field or deformation to the fluid and monitor the resultant deformation or stress. These instruments may operate in steady flow or oscillatory flow, as well as both shear and extension.

A commonly measured rheological property of a material is its shear viscosity. Shear viscosity, often referred to as simply viscosity, describes the reaction of a material to applied shear stress. In other words, shear stress is the ratio between "stress" (force per unit area) exerted on the surface of a fluid, in the lateral or horizontal direction, to the change in velocity of the fluid as you move down in the fluid (a "velocity gradient"). Volume viscosity or bulk viscosity, describes the reaction to compression and is essential for characterization of acoustics in fluids. Viscosity is preferably measured using methods known to a person skilled in the art.

Another rheological property of a material is its extensional viscosity. Extensional viscosity is the ratio of the stress required to extend a liquid in its flow direction to the extension rate. Extensional viscosity coefficients are widely used for characterizing polymers, where they cannot be simply calculated or estimated from the shear viscosity.

During processing in the mouth and swallowing, the viscosity of a food product changes due to shear forces. It is generally known that the viscosity of a food product decreases when the shear forces and rate acting on the food product (e.g., chewing forces) increase. A know treatment for beverages and liquid foods is to increase the viscosity of the food/beverage by adding starch or gum thickeners. Such thickening is thought to improve bolus control and timing of swallowing. It is, however, often disliked by patients because of the extra swallowing effort and may also leave residues at high levels of viscosity. For solid foods, pureed diets are often described when problems with mastication and swallowing of solid pieces occur in patients. However, these pureed diets may lack the natural cohesiveness that saliva provides to "real" food boluses.

Extensional viscosity is generally only relevant in flows where a fluid is "stretched"/extended (e.g., when a flowing through a constriction such as an esophageal sphincter), or when compressed (e.g., between the tongue and plate or the tongue and pharynx). However, any compressive force also implies an extension (e.g., in another direction). Only in so-called "simple shear" flows, like in a straight pipe would the shear viscosity alone determine the fluid flow. In a process like swallowing, most steps of the bolus transport will have a certain degree of extension as well. The difference between shear and extensional viscosity is usually expressed in terms of a "Trouton ratio," which is the ratio between the extensional viscosity and the shear viscosity at the same rate of deformation and as expressed in reciprocal seconds. Because of the presence of both shear and extensional forces, Applicants have found that it is important to consider the extensional viscosity and Trouton ratio of nutritional products for patients having difficulty swallowing.

As such and as opposed to the effects of shear viscosity, the nutritional products of the present disclosure aim to improve the cohesion of food boluses to prevent a food bolus from being broken up into smaller fragments, which may enter the airway or leave unwanted residues in the oropharyngeal and/or esophageal tract during the swallowing process. Salivary proteins appear to naturally have this function of increasing the cohesiveness of a food bolus. Applicants have surprisingly found that the incorporation of food grade polymers in nutritional products achieves a similar or identical, possibly even enhanced effect of increasing the cohesiveness of the food bolus (e.g., for patients who have compromised secretion of saliva). This principle may be applicable both to beverages, in which such polymers may be dissolved, and semi-solid foodstuffs (e.g., purees) which need to maintain sufficient integrity to be safely swallowed and where solid and semi-solid particles are held together by a "cohesive" aqueous phase containing such polymers.

Applicants have also found that providing inventive nutritional products to dysphagic patients having increased bolus cohesion due to its extensional viscosity, without dramatically modifying other physical properties of the material such as, for example, its shear viscosity, dramatically reduces the amount of swallowing effort for the patient, as well as the risk of residue build-up in the oropharyngeal and/or esophageal tracts. As such, products having increased cohesiveness provide improved nutritional intake of dysphagic patients by enabling them to swallow a wider variety of food and beverage products safely and comfortably. This is achieved by improving bolus integrity ("cohesiveness") and thus lending confidence to the patient in being able to consume the different products. The nutritional improvement achieved by an improved food and water intake may lead to an overall healthier condition of the patient and prevent further decline.

The polymers included in the present nutritional products may include high molecular weight, water-soluble polymers that are capable of enhancing the extensional viscosity and, thus, the cohesiveness (e.g., resistance to break-up) of the nutritional products. Such polymers include, for example, plant-extracted gums, gums produced by bacteria, high molecular weight proteins, synthetic polymers, plant-derived mucilages and chemically modified biopolymers. It is particularly preferred that plant-extracted gums and/or plant-derived mucilages are included in the present nutritional product and are as defined herein.

Thus, gums that may be used in the present nutritional products may include, for example, xanthan gum, glucomannans (konjac mannan), galactomannans (tara gum, locust bean gum, guar gum, fenugreek gum), dextran, gellan gum, tamarind gum, cassia gum, gum Arabic (acacia gum), gum ghatti, pectin, cellulosics, agar, carrageenan, alginate, tragacanth gum, karaya gum, curdlan gum, okra gum, or combinations thereof. In an embodiment, the food grade polymer is selected from the group consisting of plant-extracted gums, plant-derived mucilages and combinations thereof. The plant-extracted gums may further be selected from the group consisting of okra gum, konjac mannan, tara gum, locust bean gum, guar gum, fenugreek gum, tamarind gum, cassia gum, acacia gum, gum ghatti, pectins, cellulosics, tragacanth gum, karaya gum, or any combinations thereof. In a preferred embodiment, the plant-extracted gum is okra gum. The plant-derived mucilages may be selected from the group consisting of cactus mucilage (*Ficus indica*), psyllium mucilage (*Plantago ovata*), mallow mucilage (*Malva sylvestris*), flax seed mucilage (*Linum usitatissimum*), marshmallow mucilage (*Althaea officinalis*), ribwort mucilage (*Plantago lanceolata*), mullein mucilage (*Verbascum*), cetraria mucilage (*Lichen islandicus*), or any combinations thereof. In a preferred embodiment, the plant-derived mucilage is cactus mucilage (*Ficus indica*). It is particularly preferred that the food grade polymer is selected from okra gum and/or cactus mucilage (*Ficus indica*), or a combination thereof. In a further preferred embodiment, the plant-extracted gums and/or the inventive nutritional product do not contain starch, such as waxy maize starch, xanthan gum, modified xanthan gum such as non-pyruvylated xanthan gum or reduced-pyruvylated xanthan gum, carageenan, or a combination thereof. Preferably, it does not contain a combination of starch and carrageenan or a combination of casein and waxy maize starch.

In the context of this disclosure, xanthan gum is food grade and can be commercially obtained from numerous suppliers. Xanthan gum is a high molecular weight, long chain polysaccharide composed of the sugars glucose, mannose, and glucuronic acid. The backbone is similar to cellulose, with added side chains of trisaccharides. Galactomannans are polysaccharides made of a mannose backbone with (single) side chains of galactose units. The ratio of galactose to mannose differs in different galactomannans, with usually the majority being mannose. Glucomannans are polysaccharides mainly unbranched with a backbone comprised of D-glucose and D-mannose residues. Usually approximately 60% of the polysaccharide is made up of D-mannose and approximately 40% of D-glucose. In the context of the present disclosure, galactomannans and glucomannans are food grade and can be commercially obtained from numerous suppliers.

High molecular weight proteins may include, for example, collagen-derived proteins such as gelatin, plant proteins such as potato, pea, lupin, etc., or other proteins of sufficiently high molecular weight (MW=100 kDa and above).

Synthetic polymers must be capable of use as food additives and may include, for example, polyethyleneoxide ("PEO") or polyvinylpyrrolidone ("PVP"). PEO is a particularly useful synthetic polymer in that it is acceptable as a food grade additive and only slightly increases the shear viscosity of a composition when present in low concentrations, while also strongly enhancing the extensional viscosity and cohesiveness of a material such as, for example, water. PEO also has a relatively high Trouton ratio. PVP is also a synthetic polymer that can be used in food. There are known synergistic effects of an anionic surfactant with PVP, although the specific surfactant for which this has been demonstrated, sodium lauryl sulfate ("SDS"), cannot be used with food.

Chemically modified polymers include chemically modified biopolymers such as, but not limited to, carboxymethylcellulose.

Compositions having a high Trouton ratio generally provide enhanced extensional viscosity and, thus, enhanced cohesiveness of the products. Generally speaking most simple liquids like oils and other Newtonian fluids have a Trouton ratio of about 3. For most non-Newtonian polymer melts, the Trouton ratio is greater than 3. In an embodiment, the nutritional products of the present disclosure have a Trouton ratio that is at least about 6, preferably from about 6 to about 15. In an embodiment, the Trouton ratio is about 10. In an embodiment, the extensional viscosity of the nutritional product is greater than about 100 mPa s.

In an embodiment, the inventive nutritional products comprise a source of protein. The protein source may be dietary protein including, but not limited to animal protein (such as meat protein or egg protein), dairy protein (such as casein, caseinates (e.g., all forms including sodium, calcium, potassium caseinates), casein hydrolysates, whey (e.g., all forms including concentrate, isolate, demineralized), whey hydrolysates, milk protein concentrate, and milk protein isolate)), vegetable protein (such as soy protein, wheat protein, rice protein, and pea protein), or combinations thereof. In an embodiment, the protein source is selected from the group consisting of whey, chicken, corn, caseinate, wheat, flax, soy, carob, pea, or combinations thereof.

In an embodiment, the inventive nutritional products comprise a source of carbohydrates. Any suitable carbohydrate may be used in the present nutritional products including, but not limited to, sucrose, lactose, glucose, fructose, corn syrup solids, maltodextrin, modified starch, amylose starch, tapioca starch, corn starch or combinations thereof.

In an embodiment, the inventive nutritional products include a source of fat. The source of fat may include any suitable fat or fat mixture. For example, the fat source may include, but is not limited to, vegetable fat (such as olive oil, corn oil, sunflower oil, rapeseed oil, hazelnut oil, soy oil, palm oil, coconut oil, canola oil, lecithins, and the like), animal fats (such as milk fat) or combinations thereof.

In an embodiment, the inventive nutritional products further include one or more prebiotics. Non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, their hydrolysates, or combinations thereof.

In an embodiment, the inventive nutritional products further include one or more probiotics. Non-limiting examples of probiotics include *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or combinations thereof.

One or more amino acids may also be present in the inventive nutritional products. Non-limiting examples of amino acids include alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, or combinations thereof.

In an embodiment, the inventive nutritional products further include one or more synbiotics, sources of ω-3 fatty acids, and/or phytonutrients. As used herein, a synbiotic is a supplement that contains both a prebiotic and a probiotic that work together to improve the microflora of the intestine. Non-limiting examples of sources of ω-3 fatty acids such α-linolenic acid ("ALA"), docosahexaenoic acid ("DHA") and eicosapentaenoic acid ("EPA") include fish oil, krill, poultry, eggs, or other plant or nut sources such as flax seed, walnuts, almonds, algae, modified plants, etc. Non-limiting examples of phytonutrients include quercetin, curcumin and limonin.

One or more antioxidants may also be present in the inventive nutritional products. Non-limiting examples of antioxidants include carotenoids, coenzyme Q10 ("CoQ10"), flavonoids, glutathione Goji (wolfberry), hesperidin, lactowolfberry, lignan, lutein, lycopene, polyphenols, selenium, vitamin A, vitamin $B_1$, vitamin $B_6$, vitamin $B_{12}$, vitamin C, vitamin D, vitamin E, zeaxanthin, or combinations thereof.

The inventive nutritional products may also include fiber or a blend of different types of fiber. The fiber blend may contain a mixture of soluble and insoluble fibers. Soluble fibers may include, for example, fructooligosaccharides, acacia gum, inulin, etc. Insoluble fibers may include, for example, pea outer fiber.

The inventive nutritional products may also include other functional ingredients including chitosans and protein aggregates. Chitosans are linear polysaccharides composed of randomly distributed β-(1-4)-linked D-glucosamine (deacetylated unit) and N-acetyl-D-glucosame (acetylated unit). Among other potential benefits, chitosans have natural antibacterial properties, aid in drug delivery, and are known to rapidly clot blood. Protein aggregates are coalescences of miss-folded proteins driven by interactions between solvent-exposed hydrophobic surfaces that are normally buried within a protein's interior.

In still yet another embodiment, methods for making a nutritional product are provided, wherein the nutritional product is preferably as defined herein. The methods include providing a nutritional composition and adding a food grade polymer to the nutritional composition to form a nutritional product, preferably as defined herein, having a Trouton ratio that is at least about 6, preferably from about 6 to about 15. In an embodiment, an extensional viscosity of such product is greater than 100 mPas. In yet another embodiment, methods for improving the cohesiveness of a nutritional product are provided. The methods include adding to a nutritional composition a food grade polymer to form a nutritional product, the food grade polymer being capable of improving a cohesiveness of the nutritional composition such that the nutritional product does not break-up during consumption of the nutritional product. In an embodiment, an extensional viscosity of the product is greater than 100 mPa s. In an embodiment, a Trouton ratio of the nutritional product is at least 6, preferably from about 6 to about 15, and most preferably about 10.

In still yet another embodiment, methods for promoting safe swallowing of food boluses are provided. The methods include adding to a nutritional composition a food grade polymer to form a nutritional product, preferably as defined herein, the food grade polymer being capable of improving a cohesiveness of the nutritional composition such that the nutritional product does not break-up during consumption of the nutritional product, and administering the nutritional product to a patient in need of same. In an embodiment, an extensional viscosity of the product is greater than 100 mPas. In an embodiment, a Trouton ratio of the nutritional product is at least 6, preferably from about 6 to about 15, and most preferably about 10.

In yet another embodiment, methods for preventing and/or treating a patient having a disease as defined herein, preferably a swallowing disorder are provided. The methods include administering to a patient in need of same a nutritional product, preferably as defined herein, more preferably an effective amount of such a nutritional product, comprising a nutritional composition and a food grade polymer, the nutritional product having a Trouton ration that is at least 6, preferably from about 6 to about 15, and most preferably about 10. In an embodiment, an extensional viscosity of such product is greater than 100 mPa s. Hence, the inventive nutritional product may be used for preventing and/or treating a patient having a swallowing disorder, preferably for prevention and/or treatment of dysphagia, but also for prevention and/or treatment of malnourishment or undernourishment associated with dysphagia, preferably as mentioned above, such as e.g. silent aspiration, pneumonia, aspiration pneumonia, dehydration, pressure ulcers, etc. Treatment also may be accomplished with regard to dysphagia patients or patients highly susceptible of dysphagia or at risk of developing dysphagia, such as patients suffering from stroke, Parkinson's, Alzheimer's, Brain Damage and Multiple Sclerosis.

When treating a patient in need of such a treatment an effective amount, preferably one or more dosage units, of the inventive nutritional product may be administered suitable for the patient to be treated and depending on the specific requirements of such treatment. Such a dosage unit may have the form of a complete food, i.e. it may meet all (daily) nutritional needs of the patient, or may be a supplement or incomplete food. When provided as a supplement or incomplete food, several dosage units preferably form a complete food, e.g. 2, 3, 4 or even 5 or more. The inventive nutritional product may thus be administered either in single or in multiple dosage units per day. Multiple dosage units may be administered either in separated meals during the same meal. As a complete food, the inventive nutritional product preferably may contain from about 200 to about 3000 kcal per daily dosage/dosage unit, more preferably from about 250 to about 3000 kcal per daily dosage/dosage unit, even more preferably from about 500 to about 2500 or even from about 100 to about 2500 kcal per daily dosage/dosage unit. As an incomplete food, the inventive nutritional product preferably may contain from about 200 to about 1500 kcal per dosage unit, more preferably from about 200 to about 1000 kcal per dosage unit, even more preferably from about 200 to about 500 kcal per dosage unit. The dosage units are preferably calculated with respect to a mean daily energy supply of 2000 kcal to a healthy adult having a body weight of 70 kg. For persons of different condition and different body weight, the level is preferably adapted accordingly. Such dosage units are preferably defined as physically identifiable separate units, usually in packaged form.

In an embodiment, the food grade polymer is selected from the group consisting of plant-extracted gums, plant-derived mucilages and combinations thereof, preferably as already defined above. The plant-extracted gums are selected from the group consisting of okra gum, konjac mannan, tara gum, locust bean gum, guar gum, fenugreek gum, tamarind gum, cassia gum, acacia gum, gum ghatti, pectins, cellulosics, tragacanth gum, karaya gum, or any combinations thereof. In a preferred embodiment the plant-extracted gum is okra gum. The plant-derived mucilages may be selected from the group consisting of cactus mucilage (*Ficus indica*), psyllium mucilage (*Plantago ovata*), mallow mucilage (*Malva sylvestris*), flax seed mucilage (*Linum usitatissimum*), marshmallow mucilage (*Althaea officinalis*), ribwort mucilage (*Plantago lanceolata*), mullein mucilage (*Verbascum*), cetraria mucilage (*Lichen islandicus*), or any combinations thereof. In a preferred embodiment, the plant-derived mucilage is cactus mucilage (*Ficus indica*). It is particularly preferred that the food grade polymer is selected from okra gum and/or cactus mucilage (*Ficus indica*), or a combination thereof. In a further preferred embodiment, the plant-extracted gums and/or the inventive nutritional product do not contain starch, such as waxy maize starch, xanthan gum, modified xanthan gum such as non-pyruvylated xanthan gum or reduced-pyruvylated xanthan gum, carageenan, or a combination thereof. Preferably, it does not contain a combination of starch and carrageenan or a combination of casein and waxy maize starch.

By using the improved nutritional products as defined herein and methods of making and administering same, the nutritional intake of dysphagic patients may be improved by enabling them to swallow a wider variety of food and beverage products safely and comfortably. Such advantages may be achieved by improving the cohesiveness of a food bolus, which lends to the confidence of the patient in being able to consume a variety of products without the food bolus breaking up and possibly being aspirated by the patient. Such nutritional improvements may lead to an overall healthier condition of the patient and prevent further health-related decline.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method for treating a patient having a swallowing disorder, the method comprising:
   administering to the patient having the swallowing disorder a liquid nutritional product comprising a nutritional composition and a food grade polymer selected from the group consisting of okra gum, cactus mucilage, and combinations thereof, the liquid nutritional product having a Trouton ratio that is 6 to 15 and an extensional viscosity greater than 100 mPa s,
   wherein the liquid nutritional product comprising the food grade polymer has an increased cohesiveness relative to the nutritional composition.

2. The method according to claim 1, wherein the nutritional product has a Trouton ratio of about 10.

3. The method according to claim 1, wherein the swallowing disorder is compromised saliva excretion and/or dysphagia.

4. The method according to claim 1, wherein the nutritional product is in an administrable form selected from the group consisting of pharmaceutical formulations, nutritional formulations, dietary supplements, functional food and beverage products, and combinations thereof.

5. The method according to claim 1, wherein the food grade polymer further comprises a component is-selected from the group consisting of konjac mannan, fenugreek gum, tamarind gum, cassia gum, and combinations thereof.

6. The method according to claim 1, wherein the food grade polymer further comprises a component selected from the group consisting of mallow mucilage, flax seed mucilage, marshmallow mucilage, ribwort mucilage, mullein mucilage, cetraria mucilage, and combinations thereof.

7. The method according to claim 1, wherein the liquid nutritional product has viscoelastic properties.

\* \* \* \* \*